United States Patent
Karimi et al.

(10) Patent No.: US 7,062,009 B2
(45) Date of Patent: Jun. 13, 2006

(54) HELICAL INTERPOLATION FOR AN ASYMMETRIC MULTI-SLICE SCANNER

(75) Inventors: Seemeen S. Karimi, Brookline, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 323 days.

(21) Appl. No.: 10/659,152

(22) Filed: Sep. 10, 2003

(65) Prior Publication Data

US 2004/0165695 A1    Aug. 26, 2004

Related U.S. Application Data

(60) Provisional application No. 60/410,244, filed on Sep. 12, 2002.

(51) Int. Cl.
*G21K 1/12* (2006.01)
(52) U.S. Cl. .......................... 378/19; 378/901
(58) Field of Classification Search .................. 378/4, 378/15, 19, 901; 600/425
See application file for complete search history.

(56) References Cited

U.S. PATENT DOCUMENTS

| | | | |
|---|---|---|---|
| 6,108,575 A | 8/2000 | Besson | 600/425 |
| 6,351,514 B1 | 2/2002 | Besson | 378/15 |
| 6,415,012 B1 | 7/2002 | Taguchi et al. | 378/15 |
| 6,600,802 B1 | 7/2003 | Hsieh | 378/4 |

*Primary Examiner*—David V. Bruce
*Assistant Examiner*—Courtney Thomas
(74) *Attorney, Agent, or Firm*—McDermott Will & Emery (57) ABSTRACT

A helical interpolation filter is provided for a multi-slice scanner having an asymmetric detector array. For projection data generated in the symmetric region of the scanner, in which complementary data are available, complementary interpolation is performed. For projection data generated in the asymmetric region of the scanner, in which no complementary data are available, direct interpolation is performed. A blending region is defined near each boundary between the symmetric and the asymmetric regions. In the blending region, a combination of direct and complementary interpolation is performed.

24 Claims, 5 Drawing Sheets

HELICAL INTERPOLATION FOR AN ASYMMETRIC MULTI-SLICE SCANNER

CROSS REFERENCES TO RELATED APPLICATIONS

This application claims the benefit of priority under 35 U.S.C. §119(e) from co-pending, commonly owned U.S. provisional patent application Ser. No. 60/410,244 (entitled "Helical Interpolation For An Asymmetric Multi-Slice Scanner" and having an attorney docket number ANAK-240PR), which was filed on Sep. 12, 2002.

FIELD OF THE INVENTION

The present invention relates to CT image reconstruction. In particular, the present invention relates to helical interpolation for CT image reconstruction from asymmetric, multi-slice CT scans.

BACKGROUND

CT scans allow an image of the internal structure of a target object to be generated, one cross-sectional slice at a time. Typically, the target object is an anatomical region of a patient, although CT systems can also be used in non-medical applications, for example explosive detection. In a CT system, x-rays emitted from an x-ray source are passed through a region of the object, then are detected by a detector assembly. The detector assembly, consisting of one or more rows of detector elements, generates detection signals indicative of the attenuated intensities of the x-rays that have traversed the object. The detection signals are sent to a computer, which implements signal and image processing techniques to reconstruct a tomographic image of the object.

In a helical CT scanner, the patient is translated (typically at a constant speed), while the x-ray source and the detector assembly rotate around the patient. As the patient is moving, the data for the prescribed number of axial slices of the target region (within the patient) is acquired. Because the patient table is translated at a constant speed along the axis of rotation of the gantry during helical scanning, the image location, also called the slice plane, constantly moves in the axial direction. The trajectory of the source relative to the slice plane maps out a helix, generating projection data from which axial image slices may be reconstructed. Helical scanners offer a number of advantages, including reduced scanning time, improved image quality, and better control of contrast.

In a multi-slice helical scanner, more than one row of detector elements are arranged side-by-side along the rotation axis of the scanner. For a given view angle, it is thus possible to obtain projections that measure attenuation in multiple sections of the scanned object in a single sampling period. Multi-slice scanners are becoming the norm for medical CT applications. Multi-slice scanners make rapid acquisition of volumetric data possible, because of the larger coverage that they provide (compared to the coverage provided by single slice scanners), coupled with helical scanning. However, since in helical multi-slice scanners the patient is translated for each sample, the projections measure attenuation at different positions within the patient. This necessitates extracting consistent data sets for each cross-sectional slice position from the helical multi-slice data, in order to reconstruct each cross-sectional slice, thereby adding further complications to the image reconstruction process.

Currently, volumetric reconstruction for multi-slice scanners is typically performed by helical interpolation, followed by 2D filtered back-projection. Generally, the number of rows in multi-slice scanners is limited to about four, in order to prevent image artifacts. When the number of rows is limited to four, it has been found that helical interpolation ignoring the divergence of the x-ray beam, coupled with 2-D backprojection, is sufficient to provide clinically acceptable image quality. In this case, an interpolation filter is used to estimate virtual fan beam data for an image at a desired plane, given the positions of the plane, the source and the detector. For a larger number of rows, it has been observed that 3-D backprojection is necessary to provide acceptable image quality. Asymmetric fan beams have been used to increase a scanner's field of view (FOV) in a cost effective manner, because the FOV can be increased by increasing the number of detectors on only one side of the fan beam. When the FOV is increased in this manner, resolution is lowered in the extended part of the FOV.

All of the features described above, namely helical scanning, multiple detector rows and asymmetric fan beam, are desirable features for a CT scanner (or PET scanner), because of the advantages described above. In order to implement such an asymmetric, multi-slice, helical scanner, an appropriate image reconstruction method and system is required.

Accordingly, it is an object of the present invention to provide a method and system for CT image reconstruction, that can be used with an asymmetric multi-slice helical scanner, and that produces acceptable image quality.

SUMMARY

The present invention provides a method and system for image reconstruction from asymmetric, multi-slice helical scans. In overview, it is proposed that complementary interpolation be performed for projection data generated within the symmetric region of the x-ray beam in the multi-slice scanner, and that direct interpolation be performed for projection data generated within the asymmetric region of the x-ray beam. It is also proposed that blending regions be created near the boundaries between the symmetric and asymmetric regions, and that a combination of direct and complementary interpolation be performed in these blending regions.

A CT system in accordance with one embodiment of the present invention includes an x-ray source for generating x-rays. The x-ray source is mounted on a gantry for rotation about a rotation axis. An x-ray detector system is mounted opposite the x-ray source for providing a set of projection data with respect to the object. The CT system further includes an interpolator for interpolating the projection data from the detector array onto a slice plane by multiplying the data with helical interpolation weights. The interpolator includes an interpolation weight generator for generating the helical interpolation weights. The CT system also includes an image reconstructor for reconstructing a tomographic image of the object using the helically interpolated projection data.

The reconstructed images are perpendicular to the rotation axis, and therefore generally referred to as axial images or axial slices. The plane defined by an axial image is generally referred to as the slice plane. A plane parallel to the plane of gantry rotation is generally referred to as an axial plane.

The x-ray detector system includes a plurality of rows of detector elements. For each detector element, a corresponding detector ray is defined by x-ray photons traveling from the x-ray source to the detector element. The detector rays in a multi-slice scanner define an x-ray beam that is generally referred to as a cone beam. The cone beam of an asymmetric multi-slice scanner is asymmetric in an axial plane. The x-ray beam includes a symmetric region in which one or more complementary rays can be found for each detector ray, and an asymmetric region in which no complementary ray can be found for any detector ray. For a given detector ray, a complementary ray is defined in the present application as a detector ray whose projection on an axial plane is anti-parallel to the projection of the given detector ray on an axial plane, with the source and detector array positions reversed. Complementary rays as defined in the present application are not necessarily on parallel lines, but their projections on an axial plane substantially coincide.

A set of virtual fan beam data per slice are estimated from the helical cone beam data. For projection data resulting from detector rays lying within the symmetric region of the x-ray beam, the helical interpolation weights are called complementary interpolation weights. The complementary interpolation weights weigh complementary projection data from the different detector rows in proportion to the distance from the rows to the slice plane.

For projection data resulting from detector rays that lie within the asymmetric region of the x-ray beam, the helical interpolation weights are called direct interpolation weights. The direct interpolation weights weigh the projection data from different rows in proportion to the distance from each detector row to the slice plane.

For projection data resulting from detector rays that lie within the symmetric region of the x-ray beam but are adjacent to the asymmetric region of the x-ray beam, the helical interpolation weights are a combination of direct and complementary interpolation weights.

A method of reconstructing at least one image of an object, in accordance with one embodiment of the present invention, includes helically scanning the object with x-rays to acquire tomographic projection data representative of the object while the object is translated along an axis. The x-rays are generated by an x-ray source mounted on a gantry for rotation about the axis along which the object is translated. The x-rays are incident upon a multi-slice x-ray detector system having a plurality of substantially parallel rows of detector elements. For each detector element, a corresponding detector ray is defined by x-ray photons traveling from the x-ray source to the detector element. The detector rays define an x-ray beam that is asymmetric in the plane perpendicular to the axis of gantry rotation. The x-ray beam includes a symmetric region in which one or more complementary rays can be found for each ray, and an asymmetric region in which no complementary ray can be found for any ray.

The method further includes helically interpolating the projection data by multiplying the data with helical interpolation weights. For projection data resulting from detector rays lying within the symmetric region of the x-ray beam, the helical interpolation weights are complementary interpolation weights. For projection data resulting from detector rays that lie within the asymmetric region of the x-ray beam, the helical interpolation weights are direct interpolation weights. For projection data resulting from detector rays that lie within the symmetric region of the x-ray beam but are adjacent to the asymmetric region of the beam, the helical interpolation weights are a combination of direct and complementary interpolation weights.

The method further includes reconstructing a tomographic image of the object, using the helically interpolated projection data. In one embodiment, a 2D filtered back-projection of the helically interpolated projection data may be performed.

DESCRIPTION

The present invention is directed to a helical interpolation filter for reconstructing a tomographic image of an object, using an asymmetric, multi-slice helical CT scanner.

Figure 1:
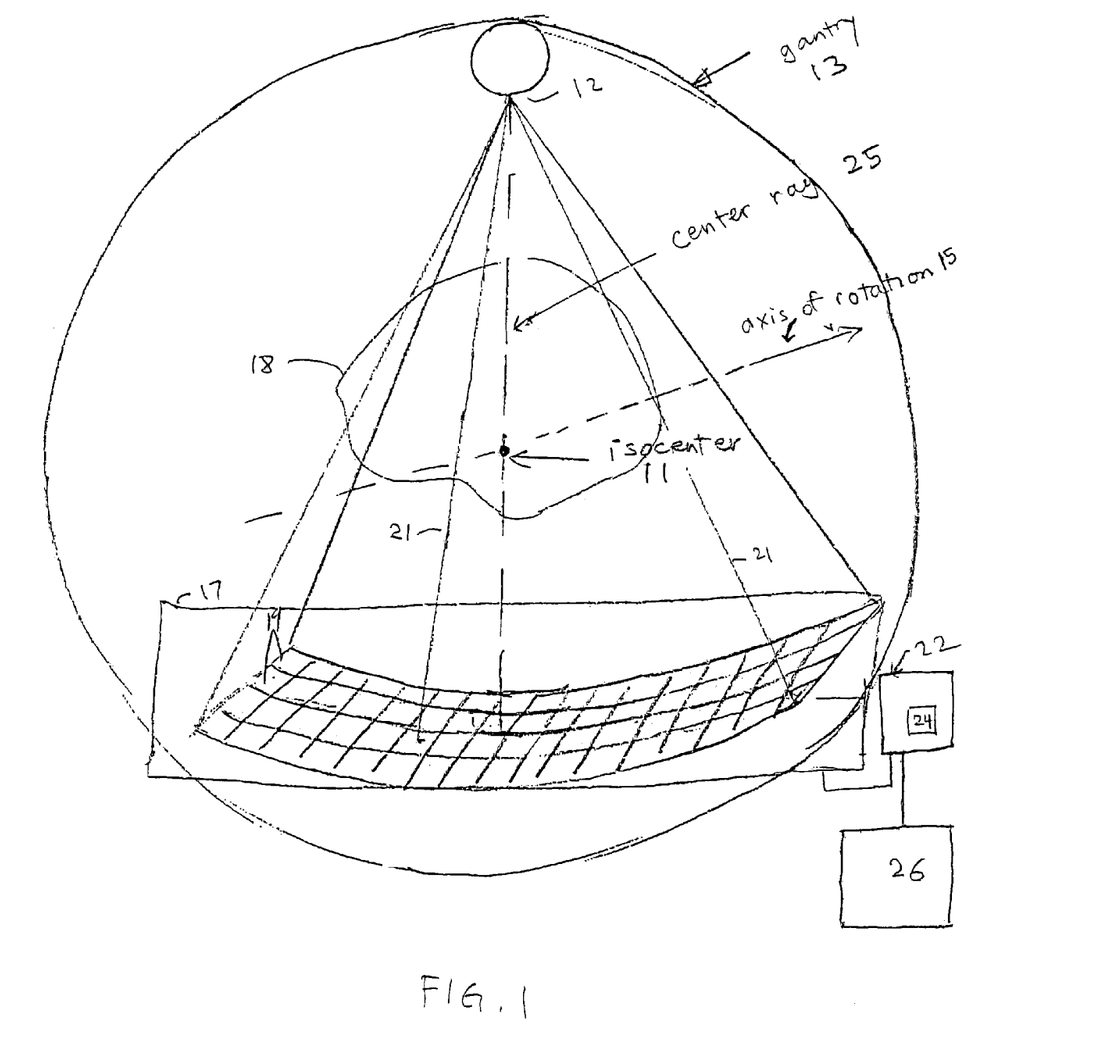
FIG. 1 illustrates a schematic block diagram of an asymmetric multi-slice CT scanner constructed in accordance with one embodiment of the present invention.

FIG. 1 illustrates a schematic block diagram of an asymmetric, multi-slice CT scanning system 10, constructed in accordance with one embodiment of the present invention. The CT scanning system 10 includes an x-ray source 12 mounted on a gantry 13 for rotation about a rotation axis 15, and an x-ray detector system 17 mounted opposite the x-ray source 12 for providing projection data with respect to an object 18, as the object 18 is translated along the rotation axis 15. The center of the circle formed by the rotation of the x-ray source 12 is the isocenter 11 of the CT system 10. The x-ray source 12 can be considered as substantially a point source. The detector system 17 includes a plurality of rows 19 of detector elements. In a multi-slice scanner, such as the CT system 10, data from multiple detector rows are used to reconstruct volume images.

For each detector element, a corresponding detector ray (or x-ray path) 21 can be defined by the x-ray photons traveling from the x-ray source to the detector element. Each detector element generates detection signals indicative of the intensity of its corresponding detector ray 21. The center ray 25 is the line from the x-ray source 12 through the isocenter 11.

Each individual row 19 of detector elements is typically configured in the shape of an arc of a circle. Preferably, the plurality of rows 19 are substantially parallel to each other, and are disposed side-by-side along the rotation axis. In this way, during a single sampling period, projection data can be acquired that are representative of a plurality of sections of the object 18.

Because each detector ray 21 is at least in part attenuated by the object it encounters in its path, the detection signal from each detector element is representative of the attenuation of the portion of the object that lies in the path of the detector ray. The raw detection signals are processed to generate a set of projection data, representative of the logarithmic attenuation effected by the mass lying in the corresponding detector ray path.

The CT system includes an interpolator 22 for interpolating the projection data from the detector array onto a slice plane, by multiplying the data with helical interpolation weights. The interpolation weights are generated by an interpolation weight generator 24, described in detail below in connection with FIG. 3. The CT system further includes an image reconstructor 26 for reconstructing a tomographic image of the object, using the helically interpolated projection data. In a preferred embodiment of the invention, the image reconstructor 26 includes means for performing 2D backprojection of the helically interpolated projection data. It should be understood, however, that image reconstruction techniques other than 2D backprojection are within the scope of the present invention, and that in alternative embodiments of the present invention, the image reconstructor 26 may include alternate means for reconstructing images from the helically interpolated projection data.

Since reconstructed images are perpendicular to the axis of rotation, they are generally referred to as axial images or axial slices. In the present application, following customary convention, the plane defined by an axial image is referred to as the slice plane. A plane parallel to the plane of gantry rotation, i.e. to the plane defined by the rotation of the gantry, is referred to as an axial plane.

Since the detector rays originate from the point x-ray source and extend at different angles to the different detector elements, the multiple detector rays resemble a cone. The collection of all the detector rays at a given instant of time is often referred to as a "cone beam." If there were a single row of detectors, then the collection of detector rays would form a "fan beam," i.e. a fan-shaped beam. The x-ray cone beam can be considered to be a collection of fan beams. In the present application, for convenience, the term "x-ray cone beam" will be used to refer to the x-ray beam defined by the collection of all the detector rays at any point in time, or at any time interval. In the present invention, the CT system is an asymmetric CT system, in which the x-ray cone beam is asymmetric in an axial plane.

Asymmetric fan beams can be used to increase a scanner's field-of-view (FOV) with lower image quality at the outer part of the FOV, by increasing the number of detectors only on one side of the fan beam. One example of a CT scanner using an asymmetric fan beam is the "A" scanner, manufactured by Analogic Corporation. In such scanners, one side of the fan beam covers the entire FOV, while the other side fails to cover a portion of the FOV. In the part of the FOV that is covered by only one side of the fan beam, the sampling frequency is reduced. The image quality is therefore compromised in this part of the FOV.

A set of virtual fan beam data per slice are estimated from the x-ray cone beam data. For each ray in the virtual fan beam, rays at the same azimuthal angle as the given fan beam ray, and complementary rays, are identified in the x-ray cone beam. The azimuthal angle is defined in this application as the angle made by the projection of a ray onto the plane of gantry rotation with a fixed axis in said plane. The interpolator interpolates projection data from different rows at these rays, to estimate the virtual fan beam data for the slice. If more than one rotation of views is used to generate one slice, then multiple projection rays and multiple complementary projection rays for a given azimuthal angle may be obtained and used.

A number of reconstruction algorithms are known for multi-slice scanners. Some algorithms are able to perform exact reconstruction, while others achieve various degrees of approximate reconstruction. Exact reconstruction techniques use 3D backprojection, while approximate algorithms may use either 3D or 2D backprojection. When the number of rows is limited to four, it has been found that helical interpolation ignoring the cone beam divergence, coupled with 2D backprojection, is sufficient to provide clinically acceptable image quality. 2D reconstruction assumes that the x-rays incident on all rows are perpendicular to the axis of rotation, ignoring the fact that the cone beam is in reality divergent. The interpolation filter 22 is used to estimate the data at the slice plane, given the positions of the plane, the source and detector.

Figure 2:
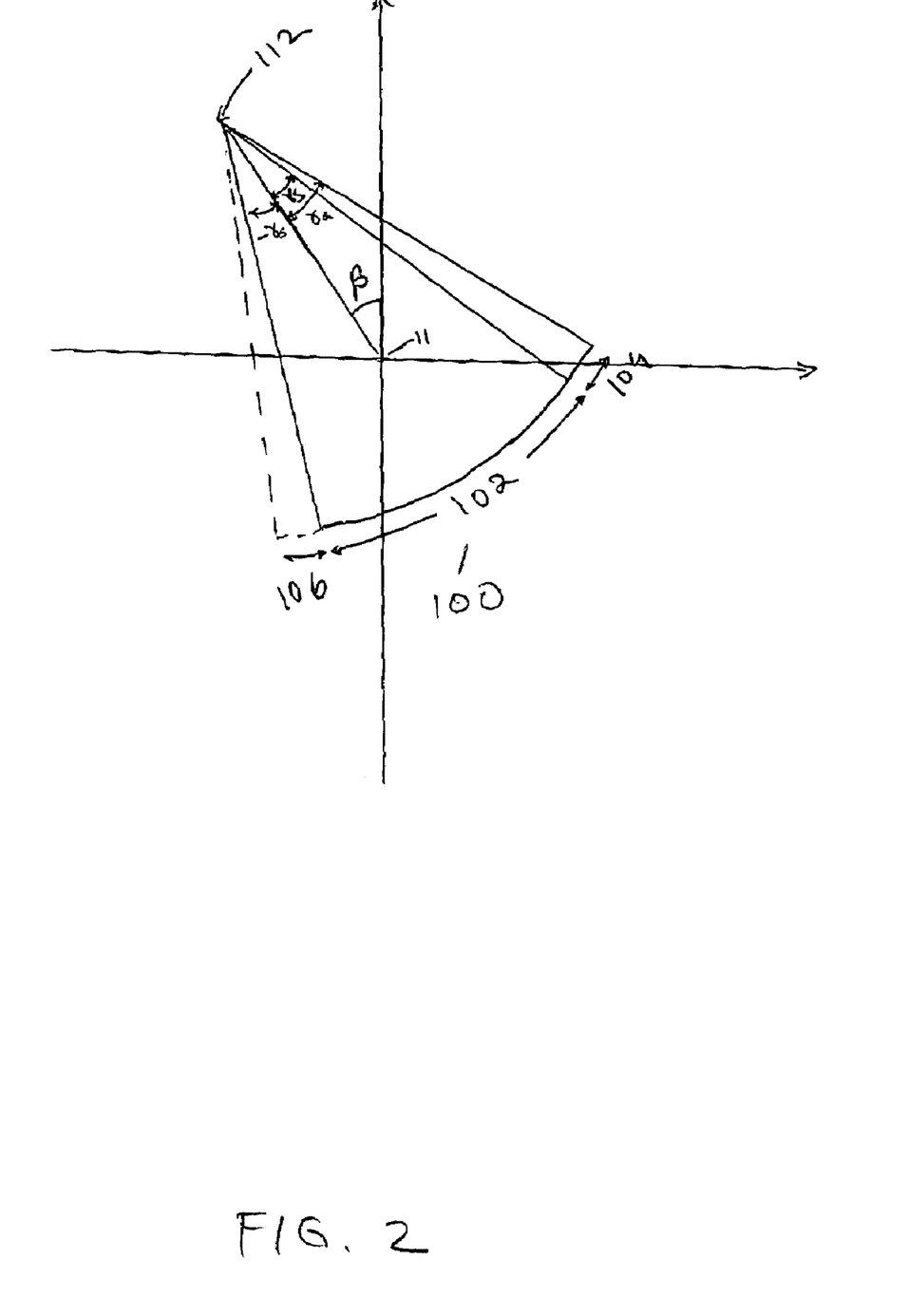
FIG. 2 illustrates an asymmetric x-ray beam, used in one embodiment of the present invention.

FIG. 2 illustrates a 2-dimensional view of an asymmetric x-ray beam 100, in an exemplary asymmetric CT scanner described in conjunction with FIG. 1. The 2-dimensional view is parallel to an axial plane, and therefore appears as a fan-shaped beam. The x-ray beam 100 includes a symmetric region 102, in which at least one complementary ray can be found for each detector ray within the symmetric region, and an asymmetric region 104, in which no complementary ray can be found for any detector ray within the asymmetric region.

For a given detector ray, a complementary ray is defined in the present application as a detector ray whose projection on an axial plane is anti-parallel to the projection of the given detector ray on an axial plane, with the source and detector array positions reversed. Complementary rays as defined in the present application are not necessarily on parallel lines, but their projections on an axial plane substantially coincide.

As illustrated in FIG. 2, there are no detector elements in region 106, thereby excluding the possibility of complementary detector ray pairs. Typically, for all detector rays lying with the symmetric region 102 of the x-ray beam, the projection data used in interpolation for complementary ray pairs may come from different ones of the multiple rows of detector elements, or from all the rows.

The azimuthal angle of the x-ray source 112 position is denoted as $\beta$ (the "fan angle"). The fan angle is defined as the angle between a line from the x-ray source (indicated in FIG. 2 by the reference numeral 112) to the isocenter of the CT system, and a fixed coordinate axis in the gantry rotation plane. The angle made by the projection of a detector ray onto an axial plane with the center ray (illustrated in FIG. 1) of the x-ray beam is denoted $\gamma$, and defined as the ray angle in this application. The value of $\gamma$ at the boundary of the symmetric region of the x-ray beam is indicated as $\gamma_s$. The value of $\gamma$ at the end of the asymmetric region of the x-ray beam is indicated as $\gamma_a$.

Figure 3:
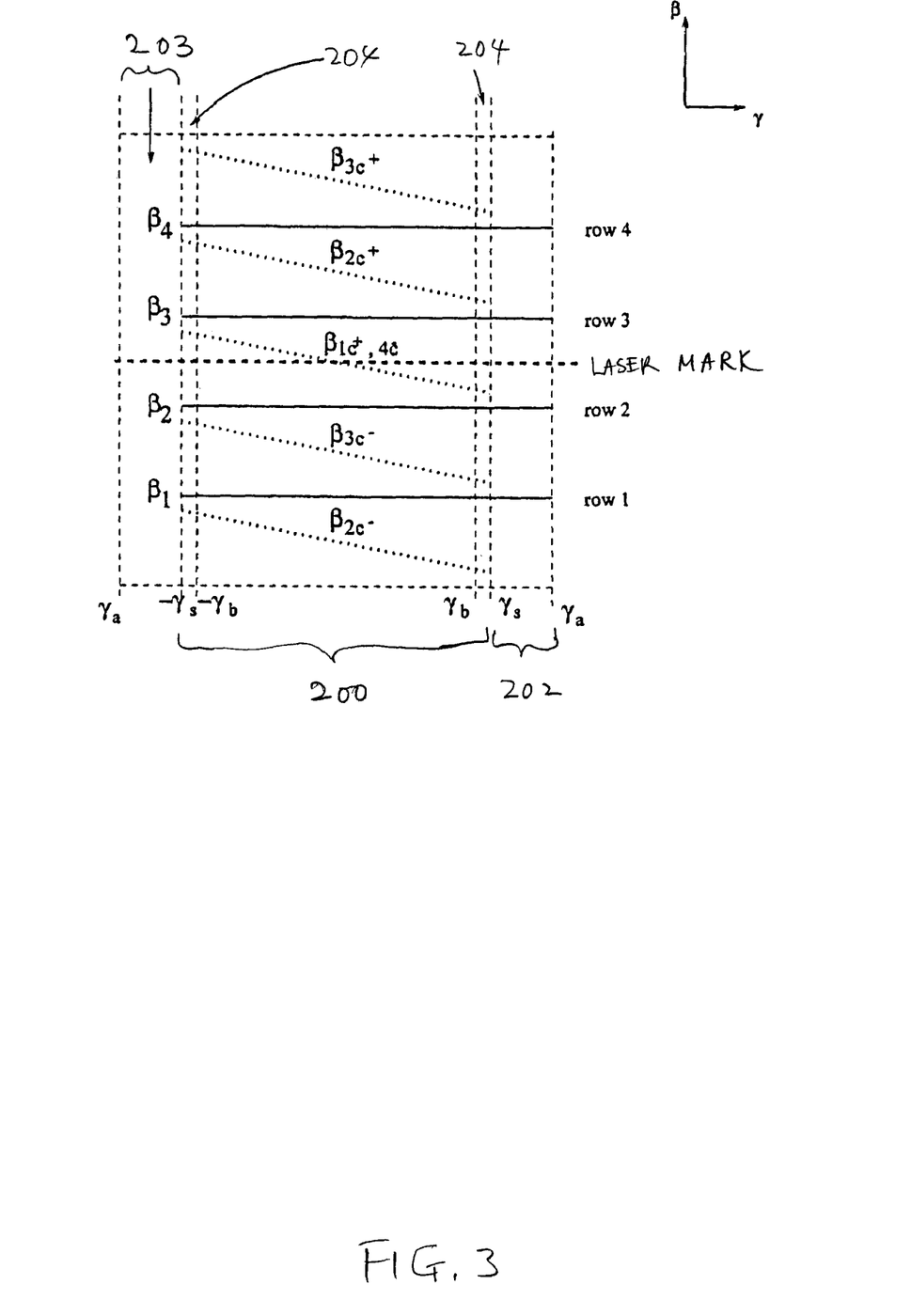
FIG. 3 illustrates a helical asymmetric interpolation filter, in accordance with one embodiment of the present invention.

Helical interpolation is implemented by creating a set of weights, and multiplying the weights by the projection data. FIG. 3 schematically illustrates a helical asymmetric interpolation filter, in accordance with one embodiment of the present invention. In the illustrated embodiment, the helical interpolation filter is designed for a four-row scanner with an asymmetric detector array; however the method and system of the present invention may be used for CT scanners having a number n of rows, where n is different from four.

FIG. 3 schematically illustrates an symmetric region 200, an asymmetric region 202, a region 203 in which no data are collected, and a pair of blending regions 204, within the asymmetric x-ray cone beam data. The symmetric region of the x-ray cone beam comprises a range $(-\gamma_s, \gamma_s)$ of ray angles, as seen in FIG. 3. The symbol $\gamma_b$ is the value of $\gamma$ at the start of the blending region within the symmetric region of the x-ray cone beam. The fan angles $\beta_i$ indicate the view angle at which the row i is directly under the slice plane at isocenter. The symbol $\beta_{ic}^{\pm}$ denotes the ray complementary to the angle $\beta_i$. It depends upon the value of $\gamma$ for each ray. The superscript indicates whether the complementary ray comes from the current rotation (+) or the previous rotation (−). The interpolation weight for each row i is denoted as $w_i$. A weight generated by complementary interpolation is labeled $w_i^c$ and a weight generated by direct interpolation is labeled $w_i^d$.

In the helical interpolation filter of the present invention, complementary interpolation is performed for data that lie within the symmetric region 200 of the x-ray cone beam, because in this region all rays have at least one complementary ray that results from reversing the positions of the source and the detector array. In the asymmetric region 202, there are no complementary rays. In this region, direct data interpolation is used.

A blending of interpolation weights across the direct and complementary interpolation portions is necessary to ensure continuity of the weights across the boundaries between the symmetric and asymmetric regions. Therefore, a blending region 204 is created near the boundary between the complementary and direct interpolation regions. In the blending regions 204, a combination of the direct and complementary interpolation is used. Since there are no complementary ray pairs in the asymmetric region 202 of the detector, blending is performed within the symmetric region 200.

For complementary interpolation, complementary ray pairs are identified for rays in the virtual fan beam. Complementary rays are related by the following equation.

$$\beta_c = \beta + \pi + 2\gamma$$

$$\gamma_c = -\gamma$$

where $\beta_c$ indicates the fan angle of the complementary ray, and $\gamma_c$ indicates its ray angle.

In general, each sample of the complementary data pair comes from different rows. The complementary interpolation weights weigh complementary projection data from different detector rows in proportion to the distance from the rows to the slice plane. Complementary rays are not truly identical, due to cone beam divergence in the axial direction. Further, due to quarter detector offset, the projection of complementary rays onto the axial plane do not truly coincide. Therefore, in the implementation of helical interpolation, the projection data are weighted according to their positions in the x-ray cone beam, but not combined.

In the illustrated preferred embodiment, the complementary interpolation weights are calculated according to the following equations, using the conventions described in $$w_1^c(\beta, \gamma) = \alpha(x_1) \begin{cases} \dfrac{\beta - \beta_{2c}^{(-)}}{\beta_1 - \beta_{2c}^{(-)}}, & \beta_{2c}^{(-)} < \beta \leq \beta_1 \\ \dfrac{\beta_{3c}^{(-)} - \beta}{\beta_{3c}^{(-)} - \beta_1}, & \beta_1 < \beta < \beta_{3c}^{(-)} \end{cases} \quad (1)$$

$$w_2^c(\beta, \gamma) = \begin{cases} \dfrac{\beta - \beta_{3c}^{(-)}}{\beta_2 - \beta_{3c}^{(-)}}, & \beta_{3c}^{(-)} < \beta \leq \beta_2 \\ \dfrac{\beta_{3c}^{(+)} - \beta}{\beta_{1c}^{(+)} - \beta_2}, & \beta_2 < \beta < \beta_{1c}^{(+)} \end{cases} \quad (2)$$

$$w_3^c(\beta, \gamma) = \begin{cases} \dfrac{\beta - \beta_{1c}^{(+)}}{\beta_3 - \beta_{1c}^{(+)}}, & \beta_{1c}^{(+)} < \beta \leq \beta_3 \\ \dfrac{\beta_{2c}^{(+)} - \beta}{\beta_{2c}^{(+)} - \beta_3}, & \beta_3 < \beta < \beta_{2c}^{(-)} \end{cases} \quad (3)$$

-continued $$w_4^c(\beta, \gamma) = (1 - \alpha(x_4)) \begin{cases} \dfrac{\beta - \beta_{2c}^{(+)}}{\beta_4 - \beta_{2c}^{(+)}}, & \beta_{2c}^{(+)} < \beta \leq \beta_4 \\ \dfrac{\beta_{3c}^{(+)} - \beta}{\beta_{3c}^{(+)} - \beta_4}, & \beta_4 < \beta < \beta_{3c}^{(+)} \end{cases} \quad (4)$$

where $$\alpha(x) = 3x^2 - 2x^3, \; x_1 = \dfrac{\beta - \beta_{2c}^{(1)}}{\beta_{3c}^{(-)} - \beta_{2c}^{(-)}} \text{ and } x_4 = \dfrac{\beta - \beta_{2c}^{+}}{\beta_{3c}^{(+)} - \beta_{2c}^{(+)}}. \quad (5)$$

The complementary weights should be independent of the absolute view angles. By way of example, in a scanner mode in which $$\beta_1 = \frac{2\pi}{3},$$

the β-values for the other rows (i=2, . . . 4) are given as follows:

$$\beta_2 = \frac{4\pi}{3},$$

$\beta_3 = 2\pi$, and $$\beta_4 = \frac{8\pi}{3}.$$

These values of $\beta_i$(i=1, . . . , 4) should be used to evaluate the weight formulas above. In this case, the range of the β variable is from 0 to $$\frac{10\pi}{3}.$$

For the asymmetric region 202 of the x-ray cone beam, direct interpolation is performed. The angular range in which direct interpolation is performed is given by $(\gamma_b, \gamma_a)$, where $\gamma_b$ is the ray angle in the symmetric region at which blending is started, as shown in FIG. 2. The symbol $\gamma_a$ is the maximum ray angle of the longer side, as shown in FIGS. 2 and 3.

Direct data interpolation means that for a ray in the virtual fan with a given source fan angle and a given ray angle, the data from at least two different rows in the x-ray cone beam are interpolated. Direct interpolation weights weigh the data from different rows at a given source fan angle and ray angle, in proportion to the distance from each detector element row to the slice plane. The disadvantage of direct data interpolation is that the sampling frequency in the axial direction is reduced and the interpolation distances are larger. This means that the slice sensitivity profile (SSP) is degraded.

In the illustrated embodiment, in which the number of detector element rows is four, the direct interpolation weights are defined by the following relationship, using the conventions described in paragraph 40:

$$w_1^d(\beta,\gamma) = \begin{cases} \alpha(x_1)\left(1 - \dfrac{\beta_1 - \beta}{\beta_2 - \beta_1}\right), & \beta_{2c}^{(-)} < \beta \le \beta_1 \\ \alpha(x_1)\dfrac{\beta_2 - \beta}{\beta_2 - \beta_1}, & \beta_1 < \beta \le B_{3c}^{(-)} \\ \dfrac{\beta_2 - \beta}{\beta_2 - \beta_1}, & \beta_{3c}^{(-)} < \beta \le \beta_2 \end{cases} \quad (6)$$

$$w_2^d(\beta,\gamma) = \begin{cases} \dfrac{\beta - \beta_1}{\beta_2 - \beta_1}, & \beta_1 < \beta \le \beta_2 \\ \dfrac{\beta_3 - \beta}{\beta_3 - \beta_2}, & \beta_2 < \beta < \beta_3 \end{cases} \quad (7)$$

$$w_3^d(\beta,\gamma) = \begin{cases} \dfrac{\beta - \beta_2}{\beta_3 - \beta_2}, & \beta_2 < \beta \le \beta_3 \\ \dfrac{\beta_4 - \beta}{\beta_4 - \beta_3}, & \beta_3 < \beta < \beta_4 \end{cases} \quad (8)$$

$$w_4^d(\beta,\gamma) = \begin{cases} \dfrac{\beta - \beta_3}{\beta_4 - \beta_3}, & \beta_3 < \beta \le \beta_{2c}^{(+)} \\ (1 - \alpha(x_4))\dfrac{\beta - \beta_3}{\beta_4 - \beta_3}, & \beta_{2c}^{(+)} < \beta \le \beta_4 \\ (1 - \alpha(x_4))\left(1 - \dfrac{\beta - \beta_4}{\beta_4 - \beta_3}\right) & \beta_4 < \beta \le \beta_{3c}^{(+)} \end{cases} \quad (9)$$

In equations (6)–(9) above, $\alpha$, $x_1$, and $x_4$ are defined as in equation (5).

As seen in FIG. 3, the blending regions 204 are defined within the symmetric region 200, one blending region being located adjacent the boundary between the symmetric region 200 and the asymmetric regions 202, the other blending region being located adjacent the boundary between the symmetric region 200 and the region 203 in which no data are collected. Blending smoothes the transition between the asymmetric and symmetric regions. Blending weights are applied within the symmetric part of the boundary, so the complementary data must also be weighted accordingly. The blending regions 204 extend between angle ranges $(\gamma_b, \gamma_s)$, and $(-\gamma_b, -\gamma_s)$, where $\gamma_b$ represents the value of $\gamma$ at the start of the blending region within the symmetric region 200 of the x-ray beam, and $\gamma_s$ represents the value of $\gamma$ at the boundary between the symmetric region 200 and the asymmetric region 202.

For projection data resulting from rays that lie within the blending regions 204, the interpolation weights are blending interpolation weights, which are a combination of direct and complementary interpolation weights. In the illustrated embodiment, the blending interpolation weights are defined by the following relationship:

within the range $(\gamma_b, \gamma_s)$, $$w_i(\beta,\gamma) = (1 - \alpha_f(x))w_i^c(\beta,\gamma) + \alpha_f(x)w_i^d(\beta,\gamma); \quad (10)$$

within the range $(-\gamma_s, -\gamma_b)$, $$w_i(\beta,\gamma) = (1 - \alpha_f(x))w_i^c(\beta,\gamma); \quad (11)$$

where $\alpha_f(x) = 3x^3 - 2x^2$ and $1 \le i \le 4$, and $$x = \frac{\gamma - \gamma_b}{\gamma_s - \gamma_b}.$$

In helical interpolation, the angular range of the data that is weighted is greater than $2\pi$. The redundant data are added so that the output data spans an angular range of $2\pi$. Rebinning the set of $2\pi$ data fills in the missing data on one side of the fan beam. The rebinning process performs tangential interpolation, providing hybrid views. Each hybrid view contains rays that are parallel in the angular direction, but are not equally spaced. Each hybrid view is added to its opposite view, located $\pi$ away. The opposite view is flipped before adding. The asymmetric data from the opposite view thus fill in the missing data in each view.

Figure 4:
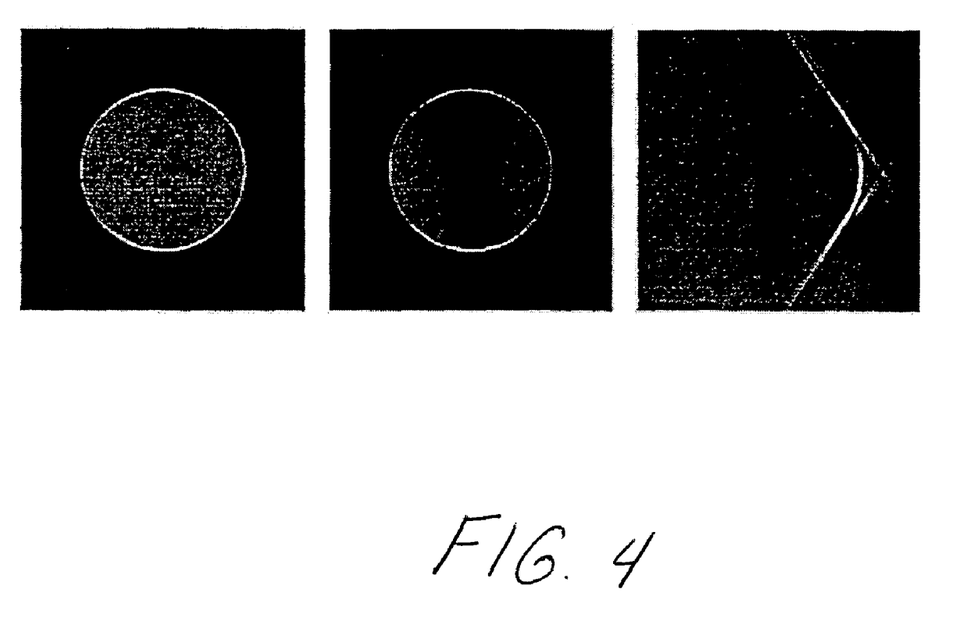
FIG. 4 illustrates a reconstructed CT image of a cylindrical phantom.

FIG. 4 illustrates a reconstructed CT image of a simulated cylinder phantom, used to test the helical interpolation filter described in connection with FIG. 3. The phantom is a cylinder whose axis is parallel to the axis of rotation. The phantom is placed at the boundary between the symmetric and asymmetric regions. For comparison, an image using a symmetric fan beam that covers the full field of view is also shown in FIG. 4.

The cylinder phantom is substantially uniform in the axial direction, so it allows us to verify whether the helical interpolation weights for each ray are correctly normalized and are continuous. FIG. 4 shows a substantially uniform attenuation within the cylinder. There are no artifacts at the boundary of the symmetric and asymmetric regions, which means that the transition is continuous, and both regions show the same CT value, which means that the normalization of weights is correct. The interpolation weights for each ray add to one.

Figure 5A:
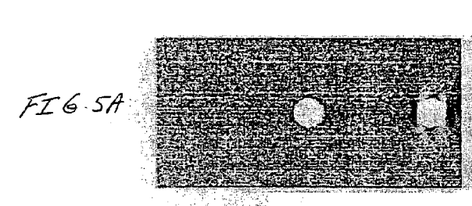
FIGS. 5A, 5B, and 5C illustrate reconstructed CT images of a phantom consisting of two spheres.
Figure 5B:
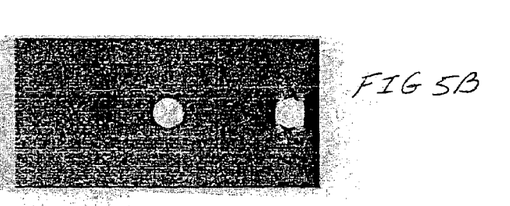
Figure 5C:
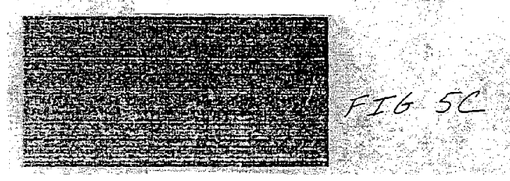

FIGS. 5A, 5B, and 5C illustrate reconstructed CT images of another phantom, used to test image quality. The phantom in each of the figures consists of two spheres of radius 30 mm. In these figures, the window width is 50 HU (Hounsfield units). The sphere at the center of the image is centered on the axis of rotation, and the other sphere in each image is centered at the boundary of the asymmetric and symmetric regions. FIG. 5A is the image produced using an asymmetric x-ray fan beam. For comparison, an image using a symmetric fan beam that covers the full field of view is also shown. FIG. 5B is the image produced using a symmetric x-ray fan beam. FIG. 5C shows the difference image. As seen from FIGS. 5A–5C, some artifacts are observed.

The artifacts in the background (as seen in FIG. 4 and in FIGS. 5A–5C) are caused by linear helical interpolation and also because the cone beam was ignored. The artifacts in the symmetric fan image are slightly smaller because complementary data extends to the extreme ends of the beam. The linear interpolation distances are smaller for the outer detector elements in the fully symmetric beam, as compared to the interpolation distances for the detector elements in the asymmetric beam. However, the artifacts from the off-center object are larger than they are from the centered object because the interpolation distances are larger than they are at isocenter, as seen in FIG. 3. At the maximum ray angle, the interpolation distance equals one, which is the same distance as in direct data interpolation.

In sum, the present invention provides a method and system for reconstructing helical, multi-slice data from an asymmetric beam. The images created using the technique of the present invention have a satisfactory image quality when tested using phantoms.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A CT system for reconstructing at least one image of an object, said system comprising:
   a. an x-ray source for generating x-rays, said x-ray source being mounted on a gantry for rotation about an axis;

b. an x-ray detector system mounted opposite said x-ray source for providing a set of projection data with respect to said object as the object is translated along said axis, said x-ray detector system including a plurality of rows of detector elements; wherein for each detector element, a corresponding detector ray is defined by x-ray photons traveling from said x-ray source to said detector element; and wherein said detector rays define an x-ray beam that is asymmetric in a plane perpendicular to said axis, said x-ray beam including a symmetric region in which one or more complementary rays can be found for each detector ray, and an asymmetric region in which no complementary ray can be found for any detector ray;

c. an interpolator for interpolating said projection data from each detector element onto a slice plane by multiplying said data with helical interpolation weights;

wherein for projection data resulting from detector rays lying within the symmetric region of said x-ray beam, the helical interpolation weights are complementary interpolation weights that weigh the data from complementary rays in proportion to the distance from each detector element row to said slice plane; and wherein for projection data resulting from detector rays that lie within the asymmetric region of said x-ray beam, the helical interpolation weights are direct interpolation weights that weigh the data at a given azimuthal angle from different rows in proportion to the distance from each detector element row to said slice plane; and d. an image reconstructor for reconstructing a tomographic image of said object using said helically interpolated projection data.

2. A CT system in accordance with claim 1, wherein said plurality of rows of detector elements are substantially parallel, and wherein said substantially parallel rows are disposed side-by-side along said axis, so that during a given sampling period, projection data can be acquired that are representative of a plurality of sections of said object.

3. A CT system in accordance with claim 1, wherein the number of said rows of detector elements is about four.

4. A CT system in accordance with claim 1, wherein for all detector rays lying within said symmetric region of said x-ray beam, the data for each detector ray and the data for its complementary rays used to interpolate the x-ray beam come from different ones of said plurality of rows of detector elements.

5. A CT system in accordance with claim 1, wherein the number of rows of detector elements is four;

wherein said rotation of said gantry defines a gantry rotation plane; and wherein said complementary interpolation weights are defined by the relationship:

$$w_1^c(\beta, \gamma) = \alpha(x_1) \begin{cases} \frac{\beta - \beta_{2c}^{(-)}}{\beta_1 - \beta_{2c}^{(-)}}, & \beta_{2c}^{(-)} < \beta \leq \beta_1 \\ \frac{\beta_{3c}^{(-)} - \beta}{\beta_{3c}^{(-)} - \beta_1}, & \beta_1 < \beta < \beta_{3c}^{(-)} \end{cases}$$

-continued $$w_2^c(\beta, \gamma) = \begin{cases} \frac{\beta - \beta_{3c}^{(-)}}{\beta_2 - \beta_{3c}^{(-)}}, & \beta_{3c}^{(-)} < \beta \leq \beta_2 \\ \frac{\beta_{3c}^{(+)} - \beta}{\beta_{1c}^{(+)} - \beta_2}, & \beta_2 < \beta < \beta_{1c}^{(+)} \end{cases}$$

$$w_3^c(\beta, \gamma) = \begin{cases} \frac{\beta - \beta_{1c}^{(+)}}{\beta_3 - \beta_{1c}^{(+)}}, & \beta_{1c}^{(+)} < \beta \leq \beta_3 \\ \frac{\beta_{2c}^{(+)} - \beta}{\beta_{2c}^{(+)} - \beta_3}, & \beta_3 < \beta < \beta_{2c}^{(-)} \end{cases}$$

$$w_4^c(\beta, \gamma) = (1 - \alpha(x_4)) \begin{cases} \frac{\beta - \beta_{2c}^{(+)}}{\beta_4 - \beta_{2c}^{(+)}}, & \beta_{2c}^{(+)} < \beta \leq \beta_4 \\ \frac{\beta_{3c}^{(+)} - \beta}{\beta_{3c}^{(+)} - \beta_4}, & \beta_4 < \beta < \beta_{3c}^{(+)} \end{cases}$$

where $\beta$ denotes the fan angle, said fan angle being defined as the angle between a line from said x-ray source to the isocenter of said CT system, and a fixed coordinate axis in said gantry rotation plane;

$\beta_i$ (i=1, . . . 4) denotes the fan angle for the i-th row indicative of the view at which the row i is directly under the point of intersection of said slice plane with said axis of rotation;

$\gamma$ denotes the angle between the projection of said detector ray on said gantry rotation plane, and a center ray disposed in the center of said x-ray beam;

$w_i^c(\beta, \gamma)$ (i=1, . . . 4) denotes the complementary interpolation weight for a detector element in the i-th row and ray angle $\gamma$ with respect to said center ray, at a fan angle $\beta$;

$\beta_{ic}$ (i=1, . . . 4) denotes the fan angle of a ray complementary to the ray at $\beta_i$, $\gamma$, (+) indicates that said complementary ray comes from a current rotation;

(−) indicates that said complementary ray comes from a previous rotation; and $$\alpha(x) = 3x^2 - 2x^3, \quad x_1 = \frac{\beta - \beta_{2c}^{(1)}}{\beta_{3c}^{(-)} - \beta_{2c}^{(-)}} \text{ and } x_4 = \frac{\beta - \beta_{2c}^+}{\beta_{3c}^{(+)} - \beta_{2c}^{(+)}}.$$

6. A CT system in accordance with claim 5, wherein the number of rows of detector elements is four, and wherein said direct interpolation weights are defined by the relationship:

$$w_1^d(\beta, \gamma) = \begin{cases} \alpha(x_1)\left(1 - \frac{\beta_1 - \beta}{\beta_2 - \beta_1}\right), & \beta_{2c}^{(-)} < \beta \leq \beta_1 \\ \alpha(x_1)\frac{\beta_2 - \beta}{\beta_2 - \beta_1}, & \beta < \beta \leq B_{3c}^{(-)} \\ \frac{\beta_2 - \beta}{\beta_2 - \beta_1}, & \beta_{3c}^{(-)} < \beta \leq \beta_2 \end{cases}$$

$$w_2^d(\beta, \gamma) = \begin{cases} \frac{\beta - \beta_1}{\beta_2 - \beta_1}, & \beta_1 < \beta \leq \beta_2 \\ \frac{\beta_3 - \beta}{\beta_3 - \beta_2}, & \beta_2 < \beta < \beta_3 \end{cases}$$

-continued $$w_3^d(\beta,\gamma) = \begin{cases} \dfrac{\beta - \beta_2}{\beta_3 - \beta_2}, & \beta_2 < \beta \le \beta_3 \\ \dfrac{\beta_4 - \beta}{\beta_4 - \beta_3}, & \beta_3 < \beta < \beta_4 \end{cases}$$

$$w_4^d(\beta,\gamma) = \begin{cases} \dfrac{\beta - \beta_3}{\beta_4 - \beta_3}, & \beta_3 < \beta \le \beta_{2c}^{(+)} \\ (1 - \alpha(x_4))\dfrac{\beta - \beta_3}{\beta_4 - \beta_3}, & \beta_{2c}^{(+)} < \beta \le \beta_4 \\ (1 - \alpha(x_4))\left(1 - \dfrac{\beta - \beta_4}{\beta_4 - \beta_3}\right) & \beta_4 < \beta \le \beta_{3c}^{(+)} \end{cases}$$

7. A CT system in accordance with claim 1, wherein said x-ray beam further comprises at least one blending region within said symmetric region adjacent to the boundary between said symmetric region and said asymmetric region, and
wherein for projection data resulting from detector rays lying within said blending region, the helical interpolation weights are blending interpolation weights created by a combination of direction and complementary interpolation weights.

8. A CT system in accordance with claim 7, wherein said blending region occurs at γ angle ranges between ($\gamma_b$, $\gamma_s$), and (−$\gamma_b$, −$\gamma_s$), where $\gamma_b$ represents the value of γ at the start of said blending region within said symmetric region of said x-ray beam, and $\gamma_s$ represents the value of γ at said boundary between said symmetric region and said asymmetric region.

9. A CT system in accordance with claim 7, wherein said blending interpolation weights are defined by the following relationship:
within the range ($\gamma_b,\gamma_s$), $w_i(\beta,\gamma)=(1-\alpha_j(x))w_i^c(\beta,\gamma)+\alpha_j(x)w_i^d(\beta,\gamma);$ within the range (−$\gamma_s$,−$\gamma_b$), $w_i(\beta,\gamma)=(1-\alpha_j(x))w_i^c(\beta,\gamma);$ where $\alpha_j(x)=3x^3-2x^2$ and $1 \le i \le 4$, and $$x = \frac{\gamma - \gamma_b}{\gamma_s - \gamma_b}.$$

10. A CT system in accordance with claim 1, wherein said image reconstructor includes means for performing 2D (two-dimensional) backprojection of said helically interpolated projection data.

11. A CT system in accordance with claim 1, wherein said x-ray beam comprises a plurality of fan-shaped beams.

12. A CT system in accordance with claim 1, wherein said translation of said object along said axis occurs at a constant speed.

13. A CT system in accordance with claim 1, wherein the angular range of the weighted projection data is greater than 2π.

14. A CT system in accordance with claim 1, wherein said helical interpolator includes an interpolation weight generator for generating said helical interpolation weights.

15. A CT system in accordance with claim 1, wherein for all detector rays lying within said symmetric region of said x-ray beam, the data for each detector ray and the data for its complementary rays used to interpolate the x-ray beam come from every one of said plurality of rows of detector elements.

16. A method of reconstructing at least one image of an object, the method comprising:
a. helically scanning said object with x-rays to acquire tomographic projection data representative of said object while said object is translated along an axis, said x-rays being generated by an x-ray source mounted on a gantry for rotation about said axis, said x-rays being incident upon a multi-slice x-ray detector system having a plurality of substantially parallel rows of detector elements;
wherein for each detector element, a corresponding detector ray is defined by x-ray photons traveling from said x-ray source to said detector element; and
wherein said detector rays define an x-ray beam that is asymmetric in a plane perpendicular to said axis, said x-ray beam including a symmetric region in which one or more complementary rays can be found for each detector ray, and an asymmetric region in which no complementary ray can be found for any detector ray;
b. helically interpolating the projection data of the detector elements by multiplying the data with helical interpolation weights;
wherein for projection data resulting from detector rays lying within the symmetric region of said x-ray beam, the helical interpolation weights are complementary interpolation weights that weigh the data from complementary rays in proportion to the distance from each detector element row to said slice plane; and
wherein for projection data resulting from detector rays that lie within the asymmetric region of said x-ray beam, the helical interpolation weights are direct interpolation weights that weigh the data at a given azimuthal angle from different rows in proportion to the distance from each detector element row to said slice plane; and
c. reconstructing a tomographic image of said object, using said helically interpolated projection data.

17. A method in accordance with claim 16, wherein said plurality of rows of detector elements are substantially parallel, and wherein said substantially parallel rows are disposed side-by-side along said axis, so that during a given sampling period, projection data can be acquired that are representative of a plurality of sections of said object.

18. A method in accordance with claim 16, wherein for all detector rays lying within said symmetric region, the data for each detector ray and the data for its complementary ray used to interpolate the x-ray beam come from different ones of said plurality of rows of detector elements.

19. A method in accordance with claim 16, wherein for all detector rays lying within said symmetric region of said x-ray beam, the data for each detector ray and the data for its complementary rays used to interpolate the x-ray beam come from every one of said plurality of rows of detector elements.

20. A method in accordance with claim 16, wherein the number of rows of detector elements is four;
wherein said rotation of said gantry defines a gantry rotation plane; and wherein said complementary interpolation weights are defined by the relationship:

$$w_1^c(\beta, \gamma) = \alpha(x_1) \begin{cases} \frac{\beta - \beta_{2c}^{(-)}}{\beta_1 - \beta_{2c}^{(-)}}, & \beta_{2c}^{(-)} < \beta \leq \beta_1 \\ \frac{\beta_{3c}^{(-)} - \beta}{\beta_{3c}^{(-)} - \beta_1}, & \beta_1 < \beta < \beta_{3c}^{(-)} \end{cases}$$

$$w_2^c(\beta, \gamma) = \begin{cases} \frac{\beta - \beta_{3c}^{(-)}}{\beta_2 - \beta_{3c}^{(-)}}, & \beta_{3c}^{(-)} < \beta \leq \beta_2 \\ \frac{\beta_{3c}^{(+)} - \beta}{\beta_{1c}^{(+)} - \beta_2}, & \beta_2 < \beta < \beta_{1c}^{(+)} \end{cases}$$

$$w_3^c(\beta, \gamma) = \begin{cases} \frac{\beta - \beta_{1c}^{(+)}}{\beta_3 - \beta_{1c}^{(+)}}, & \beta_{1c}^{(+)} < \beta \leq \beta_3 \\ \frac{\beta_{2c}^{(+)} - \beta}{\beta_{2c}^{(+)} - \beta_3}, & \beta_3 < \beta < \beta_{2c}^{(-)} \end{cases}$$

$$w_4^c(\beta, \gamma) = (1 - \alpha(x_4)) \begin{cases} \frac{\beta - \beta_{2c}^{(+)}}{\beta_4 - \beta_{2c}^{(+)}}, & \beta_{2c}^{(+)} < \beta \leq \beta_4 \\ \frac{\beta_{3c}^{(+)} - \beta}{\beta_{3c}^{(+)} - \beta_4}, & \beta_4 < \beta < \beta_{3c}^{(+)} \end{cases}$$

where β denotes the fan angle, said fan angle being defined as the angle between a line from said x-ray source to the isocenter of said CT system, and a fixed coordinate axis in said gantry rotation plane;

$\beta_i$(i=1, . . . 4) denotes the fan angle for the i-th row indicative of the view at which the row i is directly under the point of intersection of said slice plane with said axis of rotation;

γ denotes the angle between the projection of a detector ray onto said gantry rotation plane and a center ray disposed in the center of said x-ray beam;

$w_i^c(\beta, \gamma)$(i=1, . . . 4) denotes the complementary interpolation weight for a detector element in the i-th row and ray angle γ with respect to said center ray, at a fan angle β;

$\beta_{ic}$(i=1, . . . 4) denotes the fan angle of a ray complementary to the ray at $\beta_i$, γ, (+) indicates that said complementary ray comes from a current rotation;

(−) indicates that said complementary ray comes from a previous rotation; and $$\alpha(x) = 3x^2 - 2x^3, \quad x_1 = \frac{\beta - \beta_{2c}^{(1)}}{\beta_{3c}^{(-)} - \beta_{2c}^{(-)}} \text{ and } x_4 = \frac{\beta - \beta_{2c}^+}{\beta_{3c}^{(+)} - \beta_{2c}^{(+)}}.$$

21. A method in accordance with claim 20, wherein the number of rows of detector elements is four, and
wherein said direct interpolation weights are defined by the relationship:

$$w_1^d(\beta, \gamma) = \begin{cases} \alpha(x_1)\left(1 - \frac{\beta_1 - \beta}{\beta_2 - \beta_1}\right), & \beta_{2c}^{(-)} < \beta \leq \beta_1 \\ \alpha(x_1)\frac{\beta_2 - \beta}{\beta_2 - \beta_1}, & \beta < \beta \leq B_{3c}^{(-)} \\ \frac{\beta_2 - \beta}{\beta_2 - \beta_1}, & \beta_{3c}^{(-)} < \beta \leq \beta_2 \end{cases}$$

-continued $$w_2^d(\beta, \gamma) = \begin{cases} \frac{\beta - \beta_1}{\beta_2 - \beta_1}, & \beta_1 < \beta \leq \beta_2 \\ \frac{\beta_3 - \beta}{\beta_3 - \beta_2}, & \beta_2 < \beta < \beta_3 \end{cases}$$

$$w_3^d(\beta, \gamma) = \begin{cases} \frac{\beta - \beta_2}{\beta_3 - \beta_2}, & \beta_2 < \beta \leq \beta_3 \\ \frac{\beta_4 - \beta}{\beta_4 - \beta_3}, & \beta_3 < \beta < \beta_4 \end{cases}$$

$$w_4^d(\beta, \gamma) = \begin{cases} \frac{\beta - \beta_3}{\beta_4 - \beta_3}, & \beta_3 < \beta \leq \beta_{2c}^{(+)} \\ (1 - \alpha(x_4))\frac{\beta - \beta_3}{\beta_4 - \beta_3}, & \beta_{2c}^{(+)} < \beta \leq \beta_4 \\ (1 - \alpha(x_4))\left(1 - \frac{\beta - \beta_4}{\beta_4 - \beta_3}\right), & \beta_4 < \beta \leq \beta_{3c}^{(+)} \end{cases}$$

22. A method in accordance with claim 16, wherein the step of reconstructing said image of said object includes the step of performing a 2D (two-dimensional) backprojection of said helically interpolated projection data.

23. A method in accordance with claim 16, wherein said x-ray beam further comprises at least one blending region that is contained within said symmetric region and that is proximate to the boundary between said symmetric region and said asymmetric region, and wherein for projection data resulting from detector rays lying within said blending region, the helical interpolation weights are blending interpolation weights created by a combination of direct and complementary interpolation weights.

24. A method in accordance with claim 23, wherein said blending region occurs at γ angle ranges between $(\gamma_b, \gamma_s)$, and $(-\gamma_b, -\gamma_s)$, where $\gamma_b$ represents the value of γ at the start of said blending region within said symmetric region of said x-ray beam, and $\gamma_s$ represents the value of γ at said boundary between said symmetric region and said asymmetric region; and wherein said blending interpolation weights are defined by the following relationship:
within the range $(\gamma_b, \gamma_s)$, $w_i(\beta,\gamma)=(1-\alpha_f(x))w_i^c(\beta,\gamma)+\alpha_f(x)w_i^d(\beta,\gamma);$ within the range $(-\gamma_s, -\gamma_b)$, $w_i(\beta,\gamma)=(1-\alpha_f(x))w_i^c(\beta,\gamma);$ where $\alpha_f(x)=3x^3-2x^2$ and $1 \leq i \leq 4$, and $$x = \frac{\gamma - \gamma_b}{\gamma_s - \gamma_b}.$$

* * * * *